United States Patent [19]
> Lombardino

[11] Patent Number: 4,623,486

[45] Date of Patent: Nov. 18, 1986

[54] [4-SUBSTITUTED BENZOYLOXY]-N-SUBSTITUTED-2H-1,2-BENZOTHIAZINE-3-CARBOXAMIDE 1,1-DIOXIDES HAVING ANTI-ARTHRITIC ACTIVITY

[75] Inventor: Joseph G. Lombardino, Niantic, Conn.

[73] Assignee: Pfizer Inc., New York, N.Y.

[21] Appl. No.: 738,805

[22] Filed: May 29, 1985

[51] Int. Cl.$^4$ ............... C07D 417/10; C07D 279/16; A61K 31/54
[52] U.S. Cl. ..................... 514/212; 540/481; 540/599; 514/224; 544/49; 544/62; 544/107; 544/124; 544/130; 544/141; 544/145; 544/147; 544/168; 544/376; 546/256; 546/270; 546/275; 546/283; 546/284
[58] Field of Search ............ 544/49; 260/243.3; 514/225, 212, 224

[56] References Cited

U.S. PATENT DOCUMENTS

| | | | |
|---|---|---|---|
| 3,591,584 | 7/1971 | Lombardino | 260/243 |
| 3,788,324 | 1/1974 | Zinnes et al. | 260/243 |
| 3,822,258 | 7/1984 | Zinnes et al. | 260/243 R |
| 3,900,470 | 8/1975 | Rasmussen | 544/49 |
| 3,925,371 | 12/1975 | Rasmussen | 544/49 |
| 4,180,662 | 12/1979 | Pfister et al. | 544/48 |
| 4,309,427 | 1/1981 | Lombardino | 424/246 |
| 4,376,768 | 3/1983 | Ozaki et al. | 424/246 |
| 4,434,164 | 2/1984 | Lombardino | 424/246 |
| 4,461,768 | 7/1984 | Dell'Acqua et al. | 544/49 |
| 4,540,692 | 9/1985 | Ueda et al. | 544/49 |
| 4,551,452 | 11/1985 | Marfat | 544/49 |

FOREIGN PATENT DOCUMENTS

| | | |
|---|---|---|
| 85866 | 5/1983 | European Pat. Off. |
| 79639 | 5/1983 | European Pat. Off. |
| 126894 | 10/1984 | European Pat. Off. |
| 5070888 | 5/1982 | Japan |

OTHER PUBLICATIONS

J. G. Lombardino et al., "Potent Antiinflammatory N-Heterocyclic 3-Carboxamides of 4-Hydroxy-2-Methyl-2H-1,2-Benzothiazine 1,1-Dioxide", *Journal of Medicinal Chemistry*, vol 16, No. 5, p. 493 (1973).

*Primary Examiner*—Robert Gerstl
*Assistant Examiner*—Cecilia Shen
*Attorney, Agent, or Firm*—Charles J. Knuth; Peter C. Richardson

[57] ABSTRACT

Certain novel p-aminomethylbenzoyl derivatives of 4-hydroxy-2-methyl-N-(2-pyridinyl)-2H-1,2-benzothiazine-3-carboxamide 1,1-dioxide and several other closely-related known oxicams have been prepared. These particular compounds are useful in therapy as prodrug forms of the known anti-inflammatory and analgesic oxicams. Preferred member compounds include 2-methyl-4-[4-(morpholinomethyl)benzoyloxy]-N-(2-pyridinyl)-2H-1,2-benzothiazine-3-carboxamide 1,1-dioxide, 2-methyl-4-[4-(piperidinomethyl)benzoyloxy]-N-(2-pyridinyl)-2H-1,2-benzothiazine-3-carboxamide 1,1-dioxide, 2-methyl-N-(6-methyl-2-pyridinyl)-4-[4-(piperidinomethyl)benzoyloxy]-2H-1,2-benzothiazine-3-carboxamide 1,1-dioxide, 2-methyl-4-[4-(4-methylpiperazinomethyl)benzoyloxy]-N-(2-pyridinyl)-2H-1,2-benzothiazine-3-carboxamide 1,1-dioxide and 2-methyl-4-[4-(pyridiniummethyl)benzoyloxy]-N-(2-pyridinyl)-2H-1,2-benzothiazine-3-carboxamide 1,1-dioxide chloride. Methods for preparing these compounds from known starting materials are provided.

24 Claims, No Drawings

[4-SUBSTITUTED BENZOYLOXY]-N-SUBSTITUTED-2H-1,2-BENZO-THIAZINE-3-CARBOXAMIDE 1,1-DIOXIDES HAVING ANTI-ARTHRITIC ACTIVITY

BACKGROUND OF THE INVENTION

This invention relates to new and useful benzothiazine dioxide derivatives. More particularly, it is concerned with certain novel p-aminomethylbenzoyl derivatives of 4-hydroxy-2-methyl-N-(2-pyridinyl)-2H-1,2-benzothiazine-3-carboxamide 1,1-dioxide and several other closely-related oxicams, which are of special value as prodrugs in view of their unique chemotherapeutic properites.

In the past, various attempts have been made to obtain new and better anti-inflammatory agents. For the most part, these efforts have involved the synthesis and testing of various steroidal compounds such as the corticosteroids or non-steroidal substances of an acidic nature such as phenylbutazone, indomethacine and the like, including a new agent known as piroxicam. The latter substance is a member of a class of anti-inflammatory/analgesic N-heteroaryl-4-hydroxy-2-methyl-2H-1,2-benzothiazine-3-carboxamide 1,1-dioxides (known as oxicams) described and claimed in U.S. Pat. No. 3,591,584 and is specifically, 4-hydroxy-2-methyl-N-(2-pyridinyl)-2H-1,2-benzothiazine-3-carboxamide 1,1-dioxide. Other agents of this type are disclosed in U.S. Pat. Nos. 3,787,324, 3,822,258, 4,180,662 and 4,376,768. In U.S. Pat. No. 4,434,164, there is specifically described and claimed the ethylenediamine, monoethanolamine and diethanolamine salts of 4-hydroxy-2-methyl-N-(2-pyridinyl)-2H-1,2-benzothiazine-3-carboxamide 1,1-dioxide, which are particularly valuable in pharmaceutical dosage forms as non-steroidal therapeutic agents for the treatment of painful inflammatory conditions, such as those caused by rheumatoid arthritis, since they are all crystalline, non-hygroscopic, rapidly-dissolving solids with high water solubility. In U.S. Pat. No. 4,309,427, there are disclosed certain novel acyl derivatives of 4-hydroxy-2-methyl-N-(2-pyridinyl)-2H-1,2-benzothiazine-3-carboxamide 1,1-dioxide and 4-hydroxy-2-methyl-N-(6-methyl-2-pyridinyl)-2H-1,2-benzothiazine-3-carboxamide 1,1-dioxide, respectively, which are useful as non-steroidal therapeutic agents for alleviating various inflammatory conditions, including those of the skin, especially when given via the topical route of administration. However, in the continuing search for still more improved anti-inflammatory/analgesic agents, there is a need for anti-arthritic agents that are orally administrable and yet at the same time are soluble in dilute acid, stable in acid and are highly effective therapeutically when given in a single daily dose.

SUMMARY OF THE INVENTION

In accordance with the present invention, it has now been found that certain novel p-aminomethylbenzoyl derivatives of 4-hydroxy-2-methyl-N-(2-pyridinyl)-2H-1,2-benzothiazine-3-carboxamide 1,1-dioxide and several other closely-related known oxicams are useful in therapy as prodrug forms of the known anti-inflammatory and analgesic oxicams. Consequently, the compounds of this invention are useful in therapy as non-steroidal therapeutic agents for alleviating painful inflammatory conditions such as those caused by rheumatoid arthritis, for example. The novel p-aminomethylbenzoyl derivatives of this invention are of the formula:

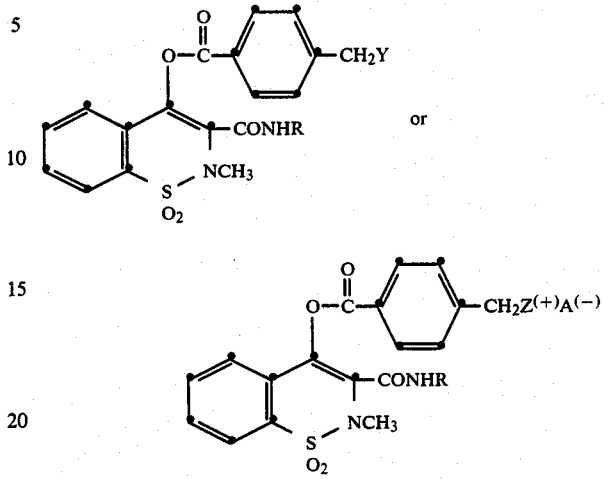

and include the pharmaceutically acceptable acid addition salts thereof, wherein R is 2-pyridyl, 6-methyl-2-pyridyl, 6-fluoro-2-pyridyl, 6-chloro-2-pyridyl, 5-methyl-3-isoxazolyl or 2-thiazolyl; Y is N,N-dialkylamino having up to three carbon atoms in each alkyl moiety, N-methyl-N-benzylamino, N-ethyl-N-benzylamino, N-methyl-N-($\beta$-phenylethyl)amino, N-ethyl-N-($\beta$-phenylethyl)amino, N-methyl-N-cycloalkylamino and N-ethyl-N-cycloalkylamino each having up to six carbon atoms in the cycloalkyl moiety, N-methyl-N-phenylamino, N-ethyl-N-phenylamino, N-methyl-N-(p-chlorophenyl)amino, N-ethyl-N-(p-chlorophenyl)amino, N-methyl-N-(N',N'-dimethylcarbamylmethyl)amino, N-methyl-N-(N',N'-diethylcarbamylmethyl)amino, pyrrolidino, piperidino, 2-methylpiperidino, 2-ethylpiperidino, homopiperidino, 1-azacyclooctyl, N-methylpiperazino, morpholino or thiomorpholino; Z is pyridinium, 2-methylpyridinium, 3-methylpyridinium, 4-methylpyridinium, 2,6-dimethylpyridinium, 2,4,6-trimethylpyridinium, 3-ethylpyridinium, 4-ethylpyridinium, 3-ethyl-4-methylpyridinium, 4-ethyl-2-methylpyridinium or 5-ethyl-2-methylpyridinium; and A is a pharmacologically acceptable anion.

All the compounds of this invention are useful in therapy, as aforesaid, as prodrug forms of the known anti-inflammatory and analgesic oxicams from which they are derived. The term "prodrug", when used in this connection, refers to compounds which are drug precursors which, following administration and absorption release the drug in vivo via some metabolic pathway or process such as hydrolysis. Accordingly, these novel compounds are particularly valuable as non-steroidal therapeutic agents for the treatment of painful inflammatory conditions, especially those caused by rheumatoid arthritis, and are particularly adapted for use in various pharmaceutical dosage forms, including those designed for oral, topical or parenteral administration. Moreover, the prodrugs of this invention are unusual in that they are readily soluble in dilute acid (and therefore readily solubilized in gastric juice), stable in acid and are highly active as anti-inflammatory/analgesic agents on the basis of a single daily dose to animals. Hence, the preferred route of administration for the presently-claimed compounds is oral, although parenteral formulations are also readily made with these soluble compounds.

Of especial interest in this connection are such typical and preferred member compounds of the invention as 2-methyl-4-[4-(morpholinomethyl)benzoyloxy]-N-(2-pyridinyl)-2H-1,2-benzothiazine-3-carboxamide 1,1-dioxide, 2-methyl-4-[4-(piperidinomethyl)benzoyloxy]-N-(2-pyridinyl)-2H-1,2-benzothiazine-3-carboxamide 1,1-dioxide, 2-methyl-N-(6-methyl-2-pyridinyl)-4-[4-(piperidinomethyl)benzoyloxy]-2H-1,2-benzothiazine-3-carboxamide 1,1-dioxide, 2-methyl-4-[4-(4-methyl-piperazinomethyl)benzoyloxy]-N-(2-pyridyl)-2H-1,2-benzothiazine-3-carboxamide 1,1-dioxide and 2-methyl-4-[4-(pyridiniummethyl)benzoyloxy]-N-(2-pyridinyl)-2H-1,2-benzothiazine-3-carboxamide 1,1-dioxide chloride, including their hydrochloride acid addition salts. These particular compounds are especially effective in treating many painful inflammatory conditions when administered by the oral or parenteral route.

DETAILED DESCRIPTION OF THE INVENTION

In the process for preparing the novel compounds of this invention, the parent oxicam compound of the formula:

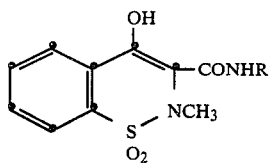

wherein R is defined as aforesaid, is treated with at least an equivalent amount in the moles of an acyl halide of the formula:

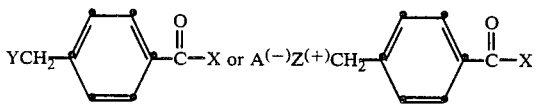

or a hydrochloride acid addition salt thereof, wherein Y, Z and A are each as previously defined and X is either chlorine or bromine. This reaction is normally carried out in a reaction-inert organic solvent under substantially anhydrous conditions in the presence of at least an equivalent amount of an appropriate standard base. In general, the reaction is conducted at a temperature of from about 0° C. up to about 50° C. for a period of about one-half to about 125 hours, although it is usually most convenient to carry out the reaction at or about room temperature after combining the reactants together at a reduced temperature, e.g., 0° to 10° C. Although any inert organic solvent may be used, it is generally most desirable to employ such solvents as aromatic hydrocarbons, halogenated lower hydrocarbons, lower alkyl ketones, lower alkyl esters of lower alkane hydrocarbon carboxylic acids, lower dialkyl ethers, dioxane and tetrahydrofuran. Preferred aromatic hydrocarbons include benzene, toluene and xylene; preferred halogenated lower hydrocarbons include methylene chloride, chloroform, ethylene dichloride and s-tetrachloroethane; preferred lower alkyl ketones include acetone, methyl ethyl ketone and methyl isobutyl ketone; preferred lower alkyl esters include methyl acetate, ethyl acetate, isopropyl acetate, methyl propionate and ethyl propionate; while preferred lower dialkyl ethers include diethyl ether, diisopropyl ether and di-n-butyl ether. Appropriate standard bases for use in this process include the alkali metal and alkaline-earth metal oxides, bicarbonates and carbonates, such as magnesium oxide, sodium bicarbonate, sodium carbonate and magnesium carbonate, as well as tertiary amines such as triethylamine, N,N-dimethylaniline and pyridine. It should be noted that the standard base employed must be present in sufficient amount to neutralize the liberated hydrogen halide formed in the reaction. Triethylamine is most preferred because it can easily be removed from the reaction mixture in the form of an insoluble solid hydrohalide precipitate.

The reaction is conveniently followed by thin-layer chromatography, thereby determining reaction times sufficient to provide complete reaction and at the same time avoiding unnecessary heating costs and excessive reaction time, which can increase the level of by-products and reduce yields.

The starting material required for preparing the novel 4-acyloxy-2-methyl-N-(2-pyridinyl)-2H-1,2-benzothiazine-3-carboxamide 1,1-dioxide derivatives of this invention are all known compounds. For instance, 4-hydroxy-2-methyl-N-(2-pyridinyl)-2H-1,1-benzothiazine-3-carboxamide 1,1-dioxide (piroxicam), 4-hydroxy-2-methyl-N-(6-methyl-2-pyridinyl)-2H-1,2-benzothiazine-3-carboxamide 1,1-dioxide and 4-hydroxy-2-methyl-N-(2-thiazolyl)-2H-1,2-benzothiazine-3-carboxamide 1,1-dioxide are all fully described in U.S. Pat. No. 3,591,584 to J. G. Lombardino, as well as in the paper to J. G. Lombardino et al., appearing in the *Journal of Medicinal Chemistry*, Vol. 16, p. 493 (1973), including their synthesis from readily available organic materials. The other closely-related oxicams required as starting materials in the process of this invention are readily available by methods well known to those skilled in the art, e.g., see the patent references to the other oxicams cited in the background section of the instant specification.

The acyl halide compounds employed as acylating agents in the herein described process of this invention, on the other hand, are themselves new compounds which are prepared by treating the corresponding 4-aminomethylbenzoic acid or a hydrohalide acid addition salt thereof with an appropriate halogenating agent like thionyl chloride or bromide, or oxalyl chloride, in accordance with the classical methods of organic synthesis as hereinafter described in the experimental section of this specification in some detail (see Preparations N-Y). The 4-aminomethylbenzoic acid compounds are, for the most part, also new compounds which are obtained by reacting the known α-chloro-p-toluylic acid with the corresponding organic amine in accordance with standard organic procedure as hereinafter described in greater detail at the beginning of experimental section of this specification (see Preparations A-M).

The oxicam prodrugs of the present invention are all readily adapted to therapeutic use as anti-arthritic agents. For instance, 2-methyl-4-[4-(piperidinomethyl)-benzoyloxy]-N-(2-pyridinyl)-2H-1,2-benzothiazine-3-carboxamide 1,1-dioxide, a typical and preferred agent of the present invention, exhibits anti-inflammatory activity in the standard carrageenin-induced rat foot edema test [described by C. A. Winter et al., *Proc. Exp. Biol. Med.*, Vol. 111, p. 544 (1962)], where it was found to cause a 47% inhibition in swelling at the 32 mg./kg. dose level when given by the oral route. The herein described p-aminomethylbenzoyl derivatives exhibit additional advantages. For instance, 2-methyl-4-[4-piperidinomethyl)benzoyloxy]-N-(2-pyridinyl)-2H-1,2-benzothiazine-3-carboxamide 1,1-dioxide has a bioavailability value of 84% in rats, is soluble in dilute acid and is also stable in dilute acid at 37° C. for a period of more than 24 hours, in addition to being highly effective as an anti-inflammatory/analgesic agent on the basis of a single daily dose to animals. The other prodrugs of this invention also afford similar results.

The herein described oxicam prodrugs of this invention can be administered via either the oral, parenteral or topical routes. In general, these compounds are most desirably administered in doses ranging from about 5.0 mg. up to about 1000 mg. per day, although variations will necessarily occur depending upon the weight and condition of the subject being treated and the particular route of administration chosen. However, a dosage level that is in the range of from about 0.08 mg. to about 16 mg. per kg. of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several smaller doses for administration throughout the day.

The oxicam prodrugs of the invention of this invention may be administered alone or in combination with pharmaceutically acceptable carriers by either of the three routes previously indicated. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 0.5% to about 90% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, gelatin and acacia. Additionally, lubricating agents such as magnesium sterarate, sodium lauryl sulfate and talc are often very useful for tabletting purposes. Solid compositions of a similar type may also be employed as fillers in gelatin capsules; preferred materials also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of these oxicam prodrugs in either sesame or peanut oil or in aqueous propylene glycol may be employed. The aqueous solutions should be suitably buffered (pH>8) if necessary and the liquid diluent first rendered isotonic. These aqueous solutions are suitable for intravenous injection purposes. The oily solutions are suitable for intra-articular, intramuscular and subcutaneous injection purposes. Additionally, it is also possible to administer the aforesaid oxicam prodrugs topically when treating inflammatory conditions of the skin or the eye and this may be preferably done by way of creams, jellies, pastes, ointments, solutions and the like, in accordance with standard pharmaceutical practice.

The anti-inflammatory activity of the compounds of the present invention is demonstrated in the previously mentioned standard carrageenin-induced rat foot edema test. In this test, anti-inflammatory activity is determined as the percent inhibition of edema formation in the hind paw of male albino rats (weighing 150-190 g.) in response to a sub-plantar injection of carrageenin. The carrageenin is injected as a 1% aqueous suspension (0.05 ml.) one hour after oral administration of the drug, which is normally given in the form of an aqueous solution. Edema formation is then assessed by measuring the volume of the injected paw initially as well as three hours after the carrageenin injection. The increase in volume three hours after carageenin injection constitutes the individual response. Compounds are considered active if the difference in response between the drug-treated animals (six rats/group) and a control group receiving the vehicle alone is significant on comparison with the results afforded by a standard compound like phenylbutazone at 33 mg./kg., via by the oral route of administration.

PREPARATION A

To a well-stirred suspension consisting of 51.2 g. (0.30 mole) of α-chloro-p-toluylic acid in 500 ml. of ethanol under a nitrogen atmosphere at room temperature (~20° C.), a solution consisting of 112.4 g. (1.32 mole) of piperidine (130.5 ml) dissolved in 100 ml. of ethanol was added dropwise over a period of 30 minutes. The resulting solution was refluxed for a period of 22.5 hours and then cooled to room temperature. The solvent was removed in vacuo to afford an amber gum. The latter material was then treated with 150 ml. of 3N aqueous sodium hydroxide to give a yellow solution and extracted three times with diethyl ether. The basic aqueous layer was chilled in an ice-water bath and acidified with 65 ml. of concentrated hydrochloric acid. This resulted in the formation of a white solid precipitate which was stirred in the cold for 15 minutes, filtered, washed with a small volume of water and air-dried overnight to give 77.71 g. of an off-white solid. Trituration of the crude product with 1500 ml. of hot isopropanol for a period of five minutes, followed by filtration and drying then gave 31.44 g. (41%) of pure 4-(piperidinomethyl)benzoic acid hydrochloride, m.p. 290°-292° C. (decomp.). Additional pure product (yield, 18.85 g.) was later recovered from the isopropanol mother liquors to bring the total yield of final product to 50.29 g. (66%). The pure product was characterized by means of thin layer chromatography, infrared absorption spectra and elemental analysis.

Anal. Calcd. for $C_{13}H_{17}NO_2.HCl$: C,61.06; H,7.09; N,5.48. Found: C,60.92; H,6.99; N,5.34.

PREPARATION B

To a well-stirred suspension consisting of 17.1 g. (0.10 mole) of α-chloro-p-toluylic acid in 200 ml. of ethanol under a nitrogen atmosphere at room temperature (~20° C.), 38.3 g. (0.44 mole) of morpholine (38.1 ml.) were added over a period of twenty minutes. The resulting reaction mixture was refluxed for a period of 23 hours and then cooled to room temperature. The solvent was removed in vacuo to give a tan solid mixed with some oil. The latter material was then treated with 100 ml. of 3N aqueous sodium hydroxide and the resulting solution subsequently extracted three times with 100 ml. of diethyl ether. The basic aqueous layer was cooled in an ice bath, acidified with concentrated hydrochloric acid and filtered to afford a tan solid (yield, 24.7 g.) melting at 271°–273° C. The solid was crystallized from ca. 300 ml. of hot ethanol to yield 11.85 g. (46%) of pure 4-(morpholinomethyl)benzoic acid hydrochloride, m.p. 274°–276° C. The pure product was characterized by means of mass spectroscopy, nuclear magnetic resonance data, thin layer chromatography and infrared absorption spectra, in addition to elemental analysis.

Anal. Calcd. for $C_{12}H_{15}NO_3.HCl$: C,55,93; H,5.87; N,5.43. Found: C,55.50; H,6.27; N,5.31.

PREPARATION C

To a well-stirred suspension consisting of 17.1 g. (0.10 mole) of α-chloro-p-toluylic acid in 150 ml. of absolute ethanol under a nitrogen atmosphere at room temperature (~20° C.), a solution consisting of 44.1 g. (0.44 mole) of N-methylpiperazine dissolved in 50 ml. of ethanol was added dropwise. The resulting reaction mixture was refluxed for a period of 16 hours and then cooled to room temperature. The cooled reaction mixture was concentrated in vacuo and the thus obtained residue partitioned between 100 ml. of diethyl ether and 100 ml. of 3N aqueous sodium hydroxide. The separated aqueous layer was then washed three times with 100 ml. of diethyl ether, cooled in an ice-water bath and subsequently acidified with concentrated hydrochloric acid. The resulting solids were filtered and air-dried, followed by trituration with 150 ml. of boiling isopropyl alcohol and stirring for a period of two minutes. After filtering while hot and drying the product there were obtained 9.4 g. (35%) of pure 4-(4-methylpiperazinomethyl)benzoic acid dihydrochloride as the hemihydrate, m.p. 310°–312° C. The pure product was characterized by means of thin layer chromatography and infrared absorption spectra, in addition to elemental analysis.

Anal. Calcd. for $C_{13}H_{18}N_2O_2.2HCl.0.5H_2O$: C,49.37; H.6.69; N,8.86. Found: C,49.41; H,6.37; N,8.70.

PREPARATION D

To a well-stirred suspension consisting of 11.9 g. (0.07 mole) of α-chloro-p-toluylic acid in 140 ml. of ethanol under a nitrogen atmosphere at room temperature (~20° C.), 17.0 g. (0.15 mole) of 2-ethylpiperidine were added dropwise over a period of twenty minutes. The resulting reaction mixture was refluxed for a period of 23 hours and then cooled to room temperature. The solvent was removed in vacuo to afford an off-white solid. This material was dissolved in 100 ml. of 3N aqueous sodium hydroxide to give a hazy solution, which was diluted with 50 ml. of water and extracted three times with 75 ml. of diethyl ether. The aqueous layer was chilled in an ice-water bath and cautiously acidified with 30 ml. of concentrated hydrochloric acid, followed by stirring in the cold for a period of 20 minutes. This resulted in the formation of a yellow oil, which was separated and dissolved in isopropanol. Concentration of the latter solution in vacuo gave a gummy white solid, which was triturated with ca. 20 ml. of ethanol to give a white solid (yield, 2.75 g.) melting at 243°–245° C. This product was designated as fraction A.

A solid eventually precipitated in the remaining aqueous layer and was collected by means of filtration to afford a pure white solid product (yield, 3.35 g.) melting at 242°–244° C. This product represented fraction B.

Fractions A and B (both slightly impure product) were then combined (total yield, 6.10 g.) and recrystallized from ca. 100 ml. of ethanol to yield 3.05 g. (15%) of pure 4-(2-ethylpiperidinomethyl)benzoic acid hydrochloride, m.p. 247°–248° C. The pure product was characterized by means of mass spectroscopy, nuclear magnetic resonance data, thin layer chromatography and infrared absorption spectra, in addition to elemental analysis.

Anal. Calcd. for $C_{15}H_{21}NO_2.HCl$: C,63.48; H,7.81; N,4.93. Found: C,63.19; H,7.76; N,5.15.

PREPARATION E

To a well-stirred suspension consisting of 11.9 g. (0.07 mole) of α-chloro-p-toluylic acid in 140 ml. of ethanol under a nitrogen atmosphere at room temperature (~20° C.), 17.5 g. (0.155 mole) of heptamethyleneimine were added over a period of twenty minutes. The resulting solution was refluxed for a period of 27.5 hours and then cooled to room temperature. It was then allowed to stand at ambient temperature for 64 hours. The solvent was removed in vacuo to afford an orange gum. The gum was treated with 100 ml. of 3N aqueous sodium hydroxide to give a hazy solution, which was extracted three times with 100 ml. of diethyl ether. The basic aqueous layer was poured over a chilled mixture consisting of 30 ml. of concentrated hydrochloric acid containing 50 g. of ice. The resulting mixture was then stirred in the cold for a period of 30 minutes, after which time an insoluble oil was observed to separate. The aqueous layer was decanted away from the oil and concentrated in vacuo to afford a waxy white solid, which was washed twice with ca. 50 ml. of ethanol and air-dried to yield 38.15 g. of an off-white solid. The solid was washed with 400 ml. of hot ethanol to remove inorganic insolubles. The ethanolic filtrate was concentrated to a volume of ca. 175 ml. and placed in a refrigerator for 16 hours to induce crystallization. The resulting pinkish-white crystalline product was then collected by means of filtration to afford 2.32 g. (12%) of pure 4-(1-azacyclooctylmethyl)benzoic acid hydrochloride as a.quarter hydrate, m.p. 224°–226° C. Additional pure product (yield, 9.85 g.) was later recovered from the ethanol mother liquors to bring the total yield of final product to 12.17 g. (61%). The pure product was characterized by means of mass spectroscopy, nuclear magnetic resonance data, thin layer chromatography and infrared absorption spectra, in addition to elemental analysis.

Anal. Calcd. for $C_{15}H_{21}NO_2.HCl.0.25H_2O$: C,62.49; H,7.87; N,4.86. Found: C,62.53; H,7.63; N,4.85.

PREPARATION F

A mixture consisting of 17.1 g. (0.10 mole) of α-chloro-p-toluylic acid, 15.0 g. (0.33 mole) of dimethylamine and 200 ml. of ethanol was placed in a 500 ml. stainless steel vessel. The sealed vessel was placed in an oil bath which had been heated to 90° C. and the entire system was heated at 85°–90° C. for 21 hours. The reaction was then chilled in an ice bath for one hour. The bomb was opened and its contents filtered to remove a small amount of insoluble white solid. The filtrate was concentrated in vacuo to give a waxy off-white solid containing a small amount of oil. The residue was dissolved in 50 ml. of 3N aqueous sodium hydroxide and extracted three times with 50 ml. of diethyl ether. The basic aqueous layer was chilled and acidified with 13.5 ml. of concentrated hydrochloric acid. The resulting slurry was then stirred in the cold for a period of 30 minutes, followed by filtration to give a beige solid (yield, 15.1 g.). This was not the desired product. The filtrate was concentrated in vacuo to afford a solid residue, which was washed with ca. 40 ml. of ethanol and dried in vacuo to yield an off-white solid substance. The solids was recrystallized from ethanol to yield 2.63 g. (12%) of pure 4-(N,N-dimethylaminomethyl)benzoic acid hydrochloride as a quarter hydrate, m.p. 225° C. (decomp.). The pure product was characterized by means of mass spectroscopy, nuclear magnetic resonance data, thin layer chromatography and infrared absorption spectra, in addition to elemental analysis.

Anal. Calcd. for $C_{10}H_{13}NO_2 \cdot HCl \cdot 0.25H_2O$: C,54.55; H,6.64; N,6.36. Found: C,54.26; H,6.61; N,6.46.

PREPARATION G

To a well-stirred suspension consisting of 17.1 g. (0.10 mole) of α-chloro-p-toluylic aid in 200 ml. of ethanol under a nitrogen atmosphere at room temperature (~20° C.), 32.2 g. (0.44 mole) of diethylamine were added dropwise over a period of 20 minutes. The resulting reaction was refluxed for a period of 17 hours and then cooled to room temperature. The solvent was removed in vacuo to give an oil-solid mixture. The latter residue was then dissolved in 50 ml. of 1N aqueous sodium hydroxide and extracted with ca. 50 ml. of diethyl ether. The basic aqueous layer was acidified with 3N hydrochloric acid to pH 3.0, followed by concentration of the resulting acidic solution under reduced pressure to ultimately afford a crude beige solid product. The product was then taken up in ca. 300 ml. of ethanol and filtered to remove insoluble sodium chloride, followed by concentration of the filtrate in vacuo to yield a crude white solid (yield, 33.5 g.). The latter material was recrystallized from ca. 50 ml. of isopropanol and filtered to afford 15.0 g. of material melting of 140°–160° C. (fraction A). An additional 1.8 g. of product was recovered from the mother liquor and this material melted at 125°–140° C. (fraction B). Fractions A and B were combined and taken up in 175 ml. of isopropanol, followed by concentration of the alcoholic solution to 125 ml. The resulting crystalline product was collected by filtration to yield 13.0 g. (54%) of pure 4-(N,N-diethylaminomethyl)benzoic acid hydrochloride, m.p. 191°–193° C. [literature m.p. 185° C., as reported in *Annalen der Chemie*, Vol. 310, p. 207 (1900)]. The pure product was characterized by means of mass spectroscopy, nuclear magnetic resonance data, thin layer chromatography and infrared absorption spectra.

PREPARATION H

To a well-stirred suspension consisting of 14.3 g. (0.084 mole) of α-chloro-p-toluylic acid in 200 ml. of absolute ethanol under a nitrogen atmosphere at room temperature (~20° C.), there were added 25 g. (0.185 mole) of N-methyl-N-(β-phenylethyl)amine dissolved in 50 ml. of absolute ethanol. The resulting reaction mixture was refluxed for a period of 18 hours and then cooled to room temperature. The cooled reaction mixture was concentrated in vacuo and the resulting residue was partitioned three times between 100 ml. of 3N aqueous sodium hydroxide and 100 ml. of diethyl ether. The basic aqueous layer was cooled in an ice bath, followed by careful acidification with concentrated hydrochloric acid to yield a white solid precipitate. The latter product was recovered by filtration and then stirred vigorously in acetonitrile for 30 minutes. After filtering the mixture and drying, there were ultimately obtained 20.26 g. (79%) of 4-[N-methyl-N-(β-phenylethyl)aminomethyl]benzoic acid hydrochloride, m.p. 268°–269° C., in the form of a white crystalline powder. The product was characterized by means of thin layer chromatography and infrared absorption spectra. It was used as such in the next reaction step without any further purification being necessary.

PREPARATION I

To a well-stirred suspension consisting of 20.0 g. (0.117 mole) of α-chloro-p-tolylic acid in 150 ml. of absolute ethanol under a nitrogen atmosphere at room temperature (~20° C.), a solution consisting of 27.7 g. (0.245 mole) of N-methyl-N-cyclohexylamine dissolved in 50 ml. of absolute ethanol was added dropwise. The resulting reaction mixture was refluxed for 20 hours and then cooled to room temperature. The cooled reaction mixture was concentrated in vacuo and the residue was partitioned between 100 ml. of diethyl ether and 100 ml. of 3N aqueous sodium hydroxide. The basic aqueous layer was then separated and extracted three times with diethyl ether and thereafter cooled in an ice-water bath, followed by careful acidification with concentrated hydrochloric acid to pH 1.0. This resulted in the formation of an oil, and the resulting oil/water system was stirred vigorously with 200 ml. of methylene chloride. A small band of oil then formed between the two layers of the aqueous organic system, and this oil was separated and thereafter triturated with diethyl ether to eventually yield a white solid product. The latter product was subsequently collected by means of suction filtration, triturated with hot isopropanol and filtered again, followed by drying to afford 13.5 g. (41%) of pure 4-(N-methyl-N-cyclohexylaminomethyl)benzoic acid hydrochloride as the hydrate, m.p. 266°–268° C. The pure product was characterized by means of thin layer chromatography and infrared absorption spectra, in addition to elemental analysis.

Anal. Calcd. for $C_{15}H_{20}NO_2 \cdot HCl \cdot H_2O$: C,59.89; H,7.37; N,4.66. Found: C,59.67; H,7.14; N,4.45.

PREPARATION J

To a well-stirred suspension consisting of 15.4 g. (0.0905 mole) of α-chloro-p-toluylic acid in 150 ml. of absolute ethanol under a nitrogen atmosphere at room temperature (~20° C.), a solution consisting of 30 g. (0.2125 mole) of 4-chloro-N-methylaniline dissolved in 50 ml. of absolute ethanol was added dropwise. The resulting mixture was refluxed for a period of 20 hours and then cooled to room temperature. The cooled reaction mixture was concentrated in vacuo and the residue was partitioned between 100 ml. of diethyl ether and 100 ml. of 3N aqueous sodium hydroxide. The basic aqueous layer was separated and extracted three times with diethyl ether and thereafter cooled in an ice-water bath, followed by careful acidification with concentrated hydrochloric acid to pH 1.0 to yield a pale-yellow white solid precipitate. The latter product was recovered by means of suction filtration and triturated with hot isopropanol, followed by further filtration and drying to ultimately afford 16.0 g (64%) of pure 4-[N-methyl-N-(p-chlorophenyl)aminomethyl]benzoic acid, m.p. 188°-191° C. The pure product was characterized by means of thin layer chromatography and infrared absorption spectra, in addition to elemental analysis.

Anal. Calcd. for $C_{15}H_{14}ClNO_2$: C,65.34; H,5.12; N,5.08. Found: ,65.28; H,5.11; N,4.98.

PREPARATION K

In a 300 ml. of four-necked, round-bottomed flask equipped with reflux condenser, mechanical stirrer, separatory funnel and thermometer, there was placed a 40% aqueous solution (61 ml.) of methylamine (24.18 g., 0.78 mole) which was chilled to 5° C. in an ice/water/-salt bath. N,N-Dimethylchloroacetamide (24.3 g., 0.20 mole) was then added dropwise to the solution over a period of 30 minutes, with the reaction temperature being maintained at 0°-10° C. throughout this step. After the addition was complete, the reaction mixture was stirred at 0°-5° C. for a period of seven hours and then placed in a refrigerator overnight ( 16 hours). The water and excess methylamine were removed by means of evaporation under reduced pressure and the pale yellow oil obtained as residue was subjected to vacuum distillation. After removing 3.4 g. of a fraction boiling at 25°-30° C./20 mm. Hg, the material in the pot solidified to a waxy off-white solid, which was recrystallized from 125 ml. of isopropanol. This product (yield, 19.5 g.) was then recrystallized from 50 ml. of ethanol. The resulting white crystalline material thus produced was collected by means of filtration and dried to ultimately afford 10.4 g. (34%) of pure N,N-dimethyl-2-methylaminoacetamide hydrochloride as a quarter hydrate, m.p. 171°-173° C. The pure product was characterized by means of mass spectroscopy, nuclear magnetic resonance data, thin layer chromatography and infrared absorption spectra, in addition to elemental analysis.

Anal. Calcd. for $C_5H_{12}N_2O.HCl.0.25H_2O$: C,38.22; H,8.66; N,17.83. Found: C,38.31; H,8.38; N, 18.01.

PREPARATION L

A solution consisting of 9.16 g. (0.06 mole) of N,N-dimethyl-2-methylaminoacetamide hydrochloride (obtained as a quarter hydrate in Preparation K) dissolved in 24 ml. of 3N aqueous sodium hydroxide was stirred at room temperature (~20° C.) for 20 minutes. The solution was concentrated in vacuo to remove the water and the residue washed three times with ca. 30 ml. of ethanol to give an oily white solid. Ethanol (40 ml.) was then added to the residue, and the resulting mixture was heated to the boiling point and thereafter filtered to remove sodium chloride.

The ethanol filtrate obtained above was added dropwise over a period of five minutes to a well-stirred suspension consisting of 4.43 g. (0.026 mole) of α-chloro-p-toluylic acid in 40 ml. of ethanol under a nitrogen atmosphere at room temperature (~20° C.). The resulting reaction mixture was stirred at room temperature for a period of ten minutes and then heated to reflux, followed by the addition of 20 ml. of ethanol and further refluxing for a period of 18.5 hours. The final reaction mixture was filtered while hot to remove insolubles and then cooled to room temperature prior to being concentrated in vacuo to give an oil/solid residue. The residue was then dissolved in 50 ml. of 3N aqueous sodium hydroxide and extracted two times with 40 ml. of diethyl ether. The basic aqueous layer was poured over 17.5 ml. of concentrated hydrochloric acid contained in ca. 35 ml. of ice-water. After chilling the mixture in an ice-water bath and filtering to remove a white solid impurity, the filtrate was concentrated in vacuo and the resulting residue washed with ca. 30 ml. of ethanol and then stripped free of solvent. The white solid so obtained was then dissolved in ca. 150 ml. of hot ethanol, filtered to remove inorganic material and the resulting filtrate evaporated under reduced pressure to yield a white solid product. The crude product was then slurried in ca. 175 ml. of hot isopropanol and filtered to afford 2.55 g. (34%) of pure 4-[N-methyl-N-(N',N'-dimethylcarbamylmethyl)aminomethyl]benzoic acid hydrochloride as the hemihydrate melting at 230° C. (decomp.). Additional pure product (yield, 1.98 g.) was later recovered from the isopropanol mother liquor to bring the total yield of final product to 4.53 g. (61%). The pure product was characterized by means of nuclear magnetic resonance data, thin layer chromatography and infrared absorption spectra, in addition to elemental analysis.

Anal. Calcd. for $C_{13}H_{18}N_2O_3.HCl.0.5H_2O$: C,52.79; H,6.82; N,9.47. Found: C,52.97; H,6.37; N,9.35.

PREPARATION M

To a well-stirred suspension consisting of 8.5 g. (0.05 mole) of α-chloro-p-toluylic acid in 100 ml. of ethanol under a nitrogen atmosphere at room temperature (~20° C.), there were added 7.9 g. (0.10 mole) of pyridine over a 15-minute period. The resulting reaction mixture was refluxed for a period of 18 hours and then cooled to room temperature. The cooled reaction mixture was filtered and the recovered product dried to ultimately afford 9.72 g. (78%) of pure 1-(4-carboxybenzyl)pyridinium chloride, m.p. 252°-253° C. The pure product was characterized by means of mass spectroscopy, nuclear magnetic resonance data, thin layer chromatography and infrared absorption spectra, in addition to elemental analysis.

Anal. Calcd. for $C_{13}H_{12}ClNO_2$: C,62.53; H,4.84; N,5.61. Found: C,62.60; H,4.87; N,5.66.

PREPARATION N

To 9.21 g. of (0.035 mole of 4-(piperidinomethyl)benzoic acid hydrochloride (the product of Preparation A) under a nitrogen atmosphere, there were added 55 ml. of thionyl chloride (89.65 g., 0.753 mole) to form a white suspension. The reaction mixture was refluxed for 2.75 hours and then cooled to room temperature (~20° C.). The resulting yellow solution was concentrated in vacuo to remove excess thionyl chloride, and the residue was washed with ca. 30 ml. of benzene and then with ca. 30 ml. of methylene chloride to give an off-white solid. The crude 4-(piperidinomethyl)benzoyl chloride hydrochloride thus obtained was used in the next reaction step without any further purification being necessary. The yield of product was assumed to be quantitative.

PREPARATION O

The 1.8 g. (0.007 mole) 4-(morpholinomethyl)benzoic acid hydrochloride (the product of Preparation B) under a nitrogen atmosphere, there were added 10 ml. of thionyl chloride (16.3 g., 0.137 mole) to form a pale-yellow mixture which was then refluxed for 22 hours. The resulting hazy yellow solution was concentrated in vacuo to remove excess thionyl chloride, and the crude white solid residue so obtained was washed with ca. 10 ml. of methylene chloride (one time) and then with ca. 10 ml. of benzene (two times) to give a white crystalline solid. In this way, there were readily obtained 1.88 g. (99%) of substantially pure 4-(morpholinomethyl)benzoyl chloride hydrochloride, m.p. 227°–230° C. (decomp.). The latter material was used in the next reaction step without any further purification being necessary. The yield of product was nearly quantitative.

PREPARATION P

To 20 g. (0.065 mole) of 4-(4-methylpiperazinomethyl)benzoic acid dihydrochloride (obtained as the hemihydrate in Preparation C) under a nitrogen atmosphere, there were added 119 ml. of thionyl chloride (194 g., 1.625 mole) to form a beige-white suspension. The reaction mixture was refluxed for 24 hours and then cooled to room temperature (~20° C.). The resulting suspension was filtered, and the recovered solids were washed with diethyl ether and dried to ultimately afford 17.0 g. (81%) of pure 4-(4-methylpiperazinomethyl)benzoyl chloride dihydrochloride, m.p. 260°–263° C.

PREPARATION Q

To a well-stirred suspension consisting of 1.4 g. (5.0 mmole) of 4-(2-ethylpiperidinomethyl)benzoic acid hydrochloride (product of Preparation D) in 25 ml. of methylene chloride under a nitrogen atmosphere, there was added dropwise over a 10-minute period a solution consisting of 1.4 g. (11.0 mmole) of oxalyl chloride dissolved in 10 ml. of methylene chloride. The resulting reaction mixture was refluxed for three hours and then cooled to room temperature (~20° C.). The cooled colorless solution was evaporated under reduced pressure, and the resulting residue was washed twice with ca. 30 ml. of benzene and then stripped free of solvent to give a white solid product. Trituration of the latter material with ca. 50 ml. of isopropyl ether, followed by filtration and drying then gave 1.55 g. of substantially pure 4-(2-ethylpiperidinomethyl)benzoyl chloride hydrochloride, m.p. 164°–166° C. The latter product was used in the next reaction step without any further purification being necessary. The yield of product was assumed to be quantitative.

PREPARATION R

To a well-stirred suspension consisting of 2.0 g. (7.0 mmole) of 4-(1-azacyclooctylmethyl)benzoic acid hydrochloride quarter-hydrate (the product of Preparation E) n 35 ml. of methylene chloride under a nitrogen atmosphere, there was added in a dropwise manner during the course of a ten-minute period a solution consisting of 1.9 g. (0.0154 mole) of oxalyl chloride dissolved in 15 ml. of methylene chloride. The resulting reaction mixture was refluxed for period of three hours and then cooled to room temperature (~20° C.). The pink solution so obtained was evaporated under reduced pressure, and the resulting residue was washed twice with ca. 30 ml. of benzene and then stripped free of solvent to give an off-white solid. Trituration of the latter material with ca. 50 ml. of isopropyl ether, followed by filtration and drying then gave 2.26 g. of substantially pure 4-(1-azacyclooctylmethyl)benzoyl chloride hydrochloride, m.p. 173°–175° C. The latter product was used as such in the next reaction step without any further purification being necessary. The yield of product was assumed to be quantitative.

PREPARATION S

To a well-stirred suspension consisting of 2.2 g. (0.01 mole) of 4-(N,N-dimethylamnomethyl)benzoic hydrochloride quarter-hydrate (the product of Preparation F) in 70 ml. of methylene chloride under a nitrogen atmosphere, there were added 2.8 g. (0.022 mole) of oxalyl chloride. The resulting reaction mixture was refluxed for 3.5 hours and then cooled to room temperature (~20° C.). The colorless solution so obtained was evaporated under reduced pressure, and the resulting residue was washed twice with ca. 40 ml. of benzene/methylene chloride (1:1 by volume) and then stripped free of solvent to give a white solid product. Trituration of the latter material with ca. 30 ml. of diethyl ether, followed by filtration and drying ultimately gave 2.15 g. (92%) of pure 4-(N,N-dimethylaminomethyl)benzoyl chloride hydrochloride, m.p. 187° C. The latter product was used as such in the next reaction step without any further purification being necessary.

PREPARATION T

To a well-stirred suspension consisting of 1.34 g. (5.0 mmole) of 4-(N,N-diethylaminomethyl)benzoic acid hydrochloride (the product of Preparation G) in 25 ml. of methylene chloride under a nitrogen atmosphere, there was added over a five-minute period a solution consisting of 1.5 g. (0.0118 mole) of oxalyl chloride dissolved in 5 ml. of methylene chloride. The resulting reaction mixture was refluxed for a period of 17 hours and then cooled to room temperature (~20° C.). The colorless solution so obtained was evaporated under reduced pressure, and the resulting residue was washed twice with methylene chloride and then stripped free of solvent to give a white solid product. In this way, there was readily obtained substantially pure 4-(N,N-diethylaminomethyl)benzoyl chloride hydrochloride, which was used in the next reaction step without any further purification being necessary. The yield of product was assumed to be quantitative.

PREPARATION U

To a well-stirred suspension consisting of 4.0 g. (0.0131 mole) of 4-[N-methyl-N-(β-phenylethyl)amino methyl]benzoic acid hydrochloride (the product of Preparation H) in 100 ml. of methylene chloride under a nitrogen atmosphere, there were added 3.49 g. (0.0275 mole) of oxalyl chloride (2.4 ml.) to form a white suspension. The latter mixture was refluxed for two hours, at which point an additional 7.28 g. (0.0574 mole) of oxalyl chloride (5 ml.) were added and refluxing was continued for an additional five hours. The suspension so obtained was concentrated to near dryness while under reduced pressure and the resulting residue azeotroped twice with benzene, followed by trituration with diethyl ether and filtration to give a white solid product. In this manner, substantially pure 4-[N-methyl-N-(β-phenylethyl)aminomethyl)benzoyl chloride hydrochloride was obtained. The latter product was used in the next reaction step without any further purification being necessary. The yield of product was assumed to be quantitative.

PREPARATION V

To 2.83 g. (0.01 mole) of 4-(N-methyl-N-cyclohexylaminomethyl)benzoic acid hydrochloride (obtained as the hydrate in Preparation I) under a nitrogen atmosphere, there were added 10.25 g. (0.10 mole) of thionyl chloride (7.3 ml.). The yellow solution was refluxed for three hours and then cooled to room temperature ($\sim 20°$ C.). The cooled reaction mixture was concentrated in vacuo and the resulting residue thereafter azeotroped twice with benzene, followed by trituration with diethyl ether to give a white solid product. After collecting the latter material by means of filtration, washing well with diethyl ether and drying, there were obtained 2.4 g. (80%) of pure N-(N-methyl-N-cyclohexylaminomethyl)benzoyl chloride hydrochloride. The latter product was used as such in the next reaction step without any further purification being necessary.

PREPARATION W

To 3.12 g. (0.011 mole) of 4-[N-methyl-N-(p-chlorophenyl)aminomethyl]benzoic acid (the product of Preparation J) under a nitrogen atmosphere, there were added 10.25 g. (0.10 mole) of thionyl chloride (7.3 ml.) to form a yellow solution. The latter mixture was then heated under reflux for a period of 2.5 hours and finally cooled to room temperature ($\sim 20°$ C.). The spent reaction mixture so obtained was then concentrated in vacuo to near dryness and the resulting residue thereafter azeotroped twice with benzene to give an oil. Trituration of the latter material with diethyl ether, followed by suction filtration and drying in vacuo to constant weight then gave 1.3 g. (36%) of pure 4-[N-methyl-N-(p-chlorophenyl)aminomethyl]benzoyl chloride hydrochloride in the form of a beige crystalline solid. The latter product was used as such in the next reaction step without any further purification being necessary.

PREPARATION X

To 1.43 g. (0.005 mole) of 4-[N-methyl-N-(N',N'-dimethylcarbamylmethylaminomethyl]benzoic acid hydrochloride (obtained as the hemihydrate in Preparation L) under a nitrogen atmosphere, there were added 15 ml. of thionyl chloride (24.45 g., 0.205 mole) to form a yellow suspension. The latter mixture wa heated under reflux for a period of 1.5 hours and then cooled to room temperature ($\sim 20°$ C.). The yellow solution so obtained was concentrated in vacuo to remove excess thionyl chloride, and the resulting residue was azeotroped twice with 10 ml. of methylene chloride to give an off-white foam. In this way, there was readily obtained substantially pure 4-[N-methyl-N-(N',N'-dimethylcarbamylmethyl)aminomethyl]benzoyl chloride hydrochloride, which was used as such in the next reaction step without any further purification being necessary. The yield of product was assumed to be quantitative.

PREPARATION Y

To 1.37 g. (0.005 mole) of 1-(4-carboxybenzyl)-pyridinium chloride (the product of Preparation M) under a nitrogen atmosphere, there were added 10 ml. of thionyl chloride (16.3 g., 0.137 mole) to form a partial solution. The latter mixture was refluxed for a period of 23.5 hours and then cooled to room temperature ($\sim 20°$ C.). The clear yellow solution so obtained was concentrated in vacuo to remove excess thionyl chloride, and the resulting residue (a yellow gum) was subsequently washed twice with ca. 50 ml. of benzene and then stripped free of solvent to give a white solid product. In this way, there was readily obtained substantially pure 1-(4-chlorocarbonylbenzyl)pyridinium chloride (m.p. 201°-203° C. with decomposition), which was used as such in the next reaction step without any further purification being necessary. The yield of product was assumed to be quantitative.

EXAMPLE 1

A stirred solution consisting of 9.94 g. (0.03 mole) of 4-hydroxy-2-methyl-N-(2-pyridinyl)-2H-1,2-benzothiozine-3-carboxamide 1,1-dioxide (prepared as described in U.S. Pat. No. 3,591,584) dissolved in 500 ml. of methylene chloride under a dry nitrogen atmosphere was chilled in an ice-water bath and treated with 10.93 g. (0.108 mole) of triethylamine (15.1 ml.), followed by the addition of 9.87 g. (0.036 mole) of 4-(piperidinomethyl)-benzoyl chloride hydrochloride (the product of Preparation N) which was added portionwise over a five-minute period. The resulting reaction mixture was stirred in the cold for a period of 15 minutes and then at room temperature ($\sim 20°$ C.) for 19.5 hours. The stirred mixture was successively extracted two times with 250 ml. of water, two times with 250 ml. of saturated aqueous sodium bicarbonate solution and one time with 250 ml. of saturated aqueous sodium chloride solution. The resulting organic layer was then dried over anhydrous sodium sulfate for a period of five hours. After removal of the drying agent by filtration and the solvent by evaporation under reduced pressure, there was finally obtained a tan solid as the crude residue. This residue was triturated with ca. 100 ml. of ethyl acetate and slurried for a period of about two hours prior to being filtered. The crude product was dissolved in 250 ml. of ethyl acetate, filtered and the resulting filtrate concentrated to a volume of ca. 175 ml. and allowed to stand at room temperature to afford a white solid product, which was subsequently filtered and dried to give 6.45 g. (44%) of pure 2-methyl-4-[4-(piperidinomethyl)benzoyloxy]-N-(2-pyridinyl)-2H-1,2-benzothiazine-3-carboxamide 1,1-dioxide, m.p. 171° C. (decomp). The pure product was characterized by means of thin layer chromatography and infrared absorption spectra, in addition to elemental analysis.

Anal. Calcd. for $C_{28}H_{28}N_4O_5S$: C, 63.14; H, 5.30; N, 10.52. Found: C, 63.08; H, 5.18; N, 10.45.

EXAMPLE 2

A stirred solution consisting of 17.3 g. (0.05 mole) of 4-hydroxy-2-methyl-N-(6-methyl-2-pyridinyl)-2H-1,2-benzothiaizne-3-carboxamide 1,1-dioxide (prepared as described in U.S. Pat. No. 3,591,584) dissolved in 850 ml. of methylene chloride under a dry nitrogen atmosphere was treated with 18.21 g. (0.18 mole) of triethylamine. This solution was cooled in an ice-water bath and then treated with 17.82 g. (0.065 mole) of N-(piperidinomethyl)benzoyl chloride hydrochloride that was added portionwise over a five-minute period. The resulting solution was stirred at 5° C. for 20 minutes and then at room temperature ($\sim 20°$ C.) for one hour. The reaction mixture was successively extracted two times with 250 ml. of water, two times with saturated aqueous sodium bicarbonate solution and one time with saturated aqueous sodium chloride solution. The resulting organic layer was then dried over anhydrous sodium sulfate, filtered and the solvent removed therefrom by means of evaporation under reduced pressure. The residue obtained was triturated with 150 ml. of ethyl acetate and filtered to yield 23.85 g. of crude product. Recrystallization of the latter material from 200 ml. of a chloroform/hexanes mixture (1:1 by volume) then gave 9.07 g. (33%) of pure 2-methyl-N-(6-methyl-2-pyridinyl)-4-[(piperidinomethyl)benzoyloxy]-2H-1,2-benzothiazine-3-carboxamide 1,1-dioxide, m.p. 178° C. (decomp.). An additional 7.4 g. (27%) yield of pure product was recovered from the filtrate. The pure product was characterized by means of thin layer chromatography and infrared absorption spectra, in addition to elemental analysis.

Anal. Calcd. for $C_{29}H_{30}N_4O_5S$: C, 63.72; H, 5.53; N, 10.25. Found: C, 63.95; H, 5.61; N, 10.47.

EXAMPLE 3

A stirred solution consisting of 6.0 g. (0.018 mole) of 4-hydroxy-2-methyl-N-(2-pyridinyl)-2H-1,2-benzothiazine-3-carboxamide 1,1-dioxide dissolved in 150 ml. of methylene chloride under a dry nitrogen atmosphere was treated with 6.07 g. (0.06 mole) of triethylamine (8.4 ml.). The resulting yellow solution was cooled in an ice-water bath, while 5.52 g. (0.02 mole) of 4-(morpholinomethyl)benzoyl chloride hydrochloride (the product of Preparation D) was added portionwise over a period of 15 minutes. An additional 50 ml. portion of methylene chloride was added to the reaction mixture, which was stirred in the cold for 30 minutes and then stirred a room temperature ($\sim 20°$ C.) for 19 hours. The stirred solution was successively extracted two times with 200 ml. of water, two times with 200 ml. of saturated aqueous sodium bicarbonate solution and one time with saturated aqueous sodium chloride. The organic layer was then dried over anhydrous sodium sulfate, filtered and the filtrate concentrated in vacuo to a bright yellow foam. The foam was triturated with 100 ml. of ethyl acetate and then filtered to give a pale yellow-white solid (yield, 4.7 g.) melting at 177° C. (decomp.). The latter material was dissolved in 200 ml. of ethyl acetate, filtered and the resulting filtrate concentrated to a volume of ca. 100 ml. and allowed to stand at room temperature. The resulting crystalline product was then collected by filtration to give a beige solid (yield, 2.65 g.) melting at 180° C. (decomp.). Further purification was then effected by recrystallizing the product from ca. 50 ml. of benzene, followed by filtering and drying to ultimately yield 1.45 g. (15%) of pure 2-methyl-4-[4-(morpholinomethyl)benzoyloxy]-N-(2-pyridinyl)-2H-1,2-benzothiazine-3-carboxamide 1,1-dioxide, m.p. 178° C. (decomp.). The pure product was characterized by means of thin layer chromatography and infrared absorption spectra, in addition to elemental analysis.

Anal. Calcd. for $C_{27}H_{26}N_4O_6S$: C, 60.66; H, 4.90; N, 10.48. Found: C, 60.52; H, 4.94; N, 10.54.

EXAMPLE 4

A stirred solution consisting of 2.07 g. (0.006 mole) of 4-hydroxy-2-methyl-N-(6-methyl-2-pyridinyl)-2H-1,2-benzothiazine-3-carboxamide 1,1-dioxide dissolved in 20 ml. of methylene chloride under a dry nitrogen atmosphere was treated with 2.00 g. (0.0198 mole) of triethylamine (2.8 ml.). The resulting solution was chilled in an ice-water bath, while a suspension consisting of 1.82 g. (0.0066 mole) of 4-(morpholinomethyl)benzoyl chloride hydrochloride in 30 ml. of methylene chloride was added over a period of 15 minutes. The resulting reaction mixture was then stirred at room temperature ($\sim 20°$ C.) for 23 hours. The stirred solution was successively extracted two times with 50 ml. of water, two times with 50 ml. of saturated aqueous sodium bicarbonate solution and one time with 50 ml. of saturated aqueous sodium chloride. The organic layer was then dried over anhydrous sodium sulfate and filtered, and the resulting filtrate concentrated in vacuo to a yellow foam which was triturated with ca. 20 ml. of ethyl acetate and slurried overnight. Filtration of the slurry then gave an off-white solid (yield, 2.56 g.), which was recrystallized from 150 ml. of hot ethyl acetate, filtered and dried to ultimately afford 1.20 g. (37%) of pure 2-methyl-N-(6-methyl-2-pyridinyl)-4-[4-(morpholinomethyl)benzoyloxy]-2H-1,2-benzothiazine-3-carboxamide 1,1-dioxide in the form of white crystals melting at 197° C. (decomp.). The pure product was characterized by means of mass spectroscopy, thin layer chromatography and infrared absorption spectra, in addition to elemental analysis.

Anal. Calcd. for $C_{28}H_{28}N_4O_6S$: C, 61.30; H, 5.14; N, 10.21. Found: C, 60.91; H, 5.10; N, 10.09.

EXAMPLE 5

A stirred solution consisting of 13.3 g. (0.040 mole) of 4-hydroxy-2-methyl-N-(2-pyridinyl)-2H-1,2-benzothiazine-3-carboxamide 1,1-dioxide dissolved in 1000 ml. of methylene chloride under a dry nitrogen atmosphere was treated with 18.4 g. (0.183 mole) of triethylamine (25.5 ml.). The resulting solution was then treated with a suspension consisting of 17 g. (0.0522 mole) of 4-(4-methylpiperazinomethyl)benzoyl chloride dihydrochloride (the product of Preparation P) in 500 ml. of methylene chloride, which was added in a portionwise manner. The resulting reaction mixture was stirred at room temperature for 18 hours. The stirred mixture was successively extracted three times with saturated aqueous sodium bicarbonate solution and one time with saturated aqueous sodium chloride, followed by drying of the organic layer over anhydrous magnesium sulfate. After removal of the drying agent by means of filtration and the solvent by means of evaporation under reduced pressure, there was obtained a residual material in the form of a yellow foam which was subsequently taken up in two liters of boiling ethyl acetate. After removal of the insolubles by means of filtration, the resulting clear filtrate was concentrated to a volume of ca. 100 ml. The resulting yellow solid product was filtered and dried to ultimately yield 6.0 g. (27%) of pure 2-methyl-4-[4-(4-methylpiperazinomethyl)benzoyloxy]-N-(2-pyridinyl)-2H-1,2-benzothiazine-3-carboxamide 1,1-dioxide as a quarter hydrate, m.p. 170°-173° C. (decomp.). The pure product was characterized by means of nuclear magnetic resonance data, thin layer chromatography and infrared absorption spectra, in addition to elemental analysis.

Anal. Calcd. for $C_{28}H_{29}N_5O_5S \cdot 0.25H_2O$: C, 60.91; H, 5.39; N, 12.69. Found: C, 60.83; H, 5.38; N, 12.34.

EXAMPLE 6

A stirred solution consisting of 2.65 g. (0.0077 mole) of 4-hydroxy-2-methyl-N-(6-methyl-2-pyridinyl)-2H-1,2-benzothiazine-3-carboxamide 1,1-dioxide dissolved in 150 ml. of methylene chloride under a dry nitrogen atmosphere was treated with 2.48 g. (0.0246 mole) of triethylamine (3.44 ml). The resulting solution was then treated with a suspension of 3.0 g. (0.0092 mole) of 4-(4-methylpiperazinomethyl)benzoyl chloride dihydrochloride in 50 ml. of methylene chloride, which was added in a portion-wise manner. The resulting reaction mixture was stirred at room temperature for approximately 18 hours. The stirred mixture was successively extracted two times with saturated aqueous sodium bicarbonate solution and one time with saturated aqueous sodium chloride, followed by drying of the organic layer over anhydrous sodium sulfate. After removal of the drying agent by filtration and the solvent by evaporation under reduced pressure, there was obtained a residual orange foam. This foam was dissolved in 500 ml. of ethyl acetate, filtered and the resulting filtrate concentrated to a volume of ca. 50 ml. and allowed to stand at room temperature. The resulting white solid product was collected by filtration and then dried to ultimately yield 800 mg. (19%) of pure 2-methyl-4-[4-(4-methylpiperazinomethyl)benzoyloxy]-N-(6-methyl-2-pyridinyl)-2H-1,2-benzothiazine-3-carboxamide 1,1-dioxide as a quarter hydrate, m.p. 176°–177° C. The pure product was characterized by means of thin layer chromatography and infrared absorption spectra, in addition to elemental analysis.

Anal. Calcd. for $C_{29}H_{31}N_5O_5S.0.25H_2O$: C, 61.52; H, 5.61; N, 12.47. Found: C, 61.37; H, 5.63; N, 12.28.

EXAMPLE 7

A stirred solution consisting of 1.32 g. (0.004 mole) of 4-hydroxy-2-methyl-N-(2-pyridinyl)-2H-1,2-benzothiazine-3-carboxamide 1,1-dioxide dissolved in 25 ml. of methylene chloride under a dry nitrogen atmosphere was treated with 1.33 g. (0.0132 mole) of triethylamine (1.84 ml.). The resulting yellow solution chilled in an ice-water bath, while a solution consisting of 1.45 g. (0.0048 mole) of 4-(2-ethylpiperidinomethyl)benzoyl chloride hydrochloride (the product of Preparation Q) dissolved in 10 ml. of methylene chloride was added dropwise over a period of ten minutes. The resulting reaction mixture was stirred at room temperature (~20° C.) for 18 hours and then heated under reflux for 24 hours. This mixture was cooled to room temperature and successively extracted two times with 40 ml. of water, two times with 40 ml. of saturated aqueous sodium bicarbonate solution and one time with 40 ml. of saturated aqueous sodium chloride. The organic layer was then dried over anhydrous sodium sulfate, filtered and the resulting filtrate concentrated in vacuo to a yellow foam which was triturated with ca. 50 ml. of diethyl ether. The resulting mixture was slurried overnight and then filtered to give a pale yellow solid (yield, 1.7 g.). The latter material was recrystallized from 30 ml. of ethyl acetate and the resulting product was collected by filtration to give a yellow solid (yield, 460 mg.). This material proved to be the desired product containing a trace of impurities, according to thin layer chromatography (TLC) analysis. Further purification was then effected by recrystallizing the material from ethyl acetate (ca. 10 ml.). The resulting yellow crystalline material was then filtered and dried to ultimately give 100 mg. (4.5%) of pure 4-[4-(2-ethylpiperdinomethyl)benzoyloxy] -2-methyl-N-(2-pyridinyl)-2H-1,2-benzothiazine-3-carboxamide 1,1-dioxide as the hemihydrate melting at 156° C. (decomp.). The pure product was characterized by means of mass spectroscopy, thin layer chromatography and infrared absorption spectra, in addition to elemental analysis.

Anal. Calcd. for $C_{30}H_{32}N_4O_5S.0.5H_2O$: C, 63.25; H, 5.84; N, 9.83. Found: C, 62.91; H, 5.73; N, 9.70.

EXAMPLE 8

A stirred solution consisting of 1.82 g. (0.0055 mole) of 4-hydroxy-2-methyl-N-(2-pyridinyl)-2H-1,2-benzothiazine-3-carboxamide 1,1-dioxide dissolved in 35 ml. of methylene chloride under a nitrogen atmosphere was treated with 1.82 g. (0.018 mole) of triethylamine (2.5 ml.). The resulting yellow solution was chilled in an ice-water bath, while a solution consisting of 2.02 g. (0.0066 mole) of 4-(1-azacyclooctylmethyl)benzoyl chloride hydrochloride (the product of Preparation R) dissolved in 15 ml. of methylene chloride was added dropwise over a period of 15 minutes. The resulting reaction solution was stirred at room temperature (~20° C.) for 40 hours. The stirred mixture was successively extracted two times with 50 ml. of water, two times with 50 ml. of saturated aqueous sodium bicarbonate solution and one time with 50 ml. of saturated aqueous sodium chloride. The organic layer was then dried over anhydrous sodium sulfate, filtered and the resulting filtrate concentrated in vacuo to a yellow foam which was thereafter triturated with ca. 75 ml. of diethyl ether. The resulting mixture was slurried overnight and then filtered to give a yellow solid (yield, 2.25 g.). The latter material was dissolved in 150 ml. of cyclohexane and filtered to remove insoluble material, followed by concentration of the resulting filtrate to a volume of ca. 75 ml. After allowing the concentrated filtrate to stand at room temperature, there was obtained a pale yellow solid which was filtered and dried to ultimately yield 480 mg. (16%) of pure 4-[4-(1-azacyclooctylmethyl)benzoyloxy]-2-methyl-N-(2-pyridinyl)-2H-1,2-benzothiazine-3-carboxamide 1,1-dioxide as the monohydrate melting at 163° C. (decomp.). The pure product was characterized by mass spectroscopy and infrared absorption spectra, in addition to elemental analysis.

Anal. Calcd. for $C_{30}H_{32}N_4O_5S.H_2O$: C, 62.27; H, 5.92; N, 9.68. Found: C, 61.82; H, 5.77; N, 9.35.

EXAMPLE 9

A stirred solution consisting of 2.65 g. (0.008 mole) of 4-hydroxy-2-methyl-N-(2-pyridinyl)-2H-1,2-benzothiazine-3-carboxamide 1,1-dioxide dissolved in 35 ml. of methylene chloride under a dry nitrogen atmosphere was treated with 2.67 g. (0.0264 mole) of triethylamine (3.7 ml). The resulting clear yellow solution was then chilled in an ice-water bath, while a suspension consisting of 2.15 g. (0.0092 mole) of 4-(N,N-dimethylaminomethyl)benzoyl chloride hydrochloride (the product of Preparation S) in 40 ml. of methylene chloride was added over a ten-minute period. The resulting reaction solution was stirred at room temperature (~20° C.) for 41 hours. The stirred reaction mixture was successively extracted one time with 60 ml. of water, two times with 60 ml. of saturated aqueous sodium bicarbonate solution and one time with 60 ml. of saturated aqueous sodium chloride. The organic layer was then dried over anhydrous sodium sulfate, filtered and the resulting filtrate concentrated in vacuo to give a yellow foam. This residue was triturated with 30 ml. of ethyl acetate and slurried for three hours, followed by filtration to give a pale yellow solid (yield, 1.6 g.). The solid was recrystallized from 75 ml. of ethyl acetate. The resulting off-white crystalline material was collected by filtration and dried to ultimately yield 600 mg.

(15%) of pure 4-[4-(N,N-dimethylaminomethyl)benzoyloxy]-2-methyl-2H-1,2-benzothiazine-3-carboxamide 1,1-dioxide, m.p. 173° C. (decomp.). The pure product was characterized by means of mass spectroscopy and infrared absorption spectra, in addition to elemental analysis.

Anal. Calcd. for $C_{25}H_{24}N_4O_5S$: C, 60.96; H, 4.91; N, 11.37. Found: C, 60.40; H, 4.91; N, 11.28.

EXAMPLE 10

A stirred solution consisting of 1.7 g. (0.005 mole) of 4-hydroxy-2-methyl-N-(2-pyridinyl)-2H-1,2-benzothiazine-3-carboxamide 1,1-dioxide dissolved in 20 ml. of methylene chloride under a dry nitrogen atmosphere was treated with 556 mg. (0.0055 mole) of triethylamine (0.40 ml.). The resulting yellow solution was chilled in an ice-water bath, while a solution consisting of 1.44 g. (0.0055 mole) of 4-(N,N-diethylaminomethyl)benzoyl chloride hydrochloride (the product of Preparation T) dissolved in 20 ml. of methylene chloride was added dropwise over a 20-minute period. The resulting reaction mixture was stirred at room temperature ($\sim 20°$ C.) for 120 hours and then concentrated in vacuo to afford a yellow foam. This residue was triturated with ca. 25 ml. of ethyl acetate and slurried overnight ($\sim 16$ hours), followed by filtration to give an off-white solid (yield, 5.2 g.). The solid was recrystallized from 30 ml. of ethanol. The resulting off-white crystalline material was filtered and dried to afford 1.1 g. of solid melting at 128°-133° C. (decomp.). The solid was then dissolved in 300 ml. of ethyl acetate, followed by concentration of the resulting filtrate to a volume of ca. 150 ml. The organic concentrate was then allowed to stand at room temperature overnight, and the resulting white crystalline material was filtered and dried to ultimately yield 410 mg. (14%) of pure 4-[4-(N,N-diethylaminomethyl)benzoyloxy]-2-methyl-2H-1,2-benzothiazine-3-carboxamide 1,1-dioxide hydrochloride as the hemihydrate melting at 181°-183° C. (decomp.). The pure product was characterized by means of mass spectroscopy, thin layer chromatography and infrared absorption spectra, in addition to elemental analysis.

Anal. Calcd. for $C_{27}H_{28}N_4O_5S \cdot HCl \cdot 0.5H_2O$ C, 57,29; H, 5.34; N, 9.90. Found: C, 57.45; H, 5.25; N, 9.82.

EXAMPLE 11

A stirred solution consisting of 3.0 g. (0.009 mole) of 4-hydroxy-2-methyl-N-(2-pyridinyl)-2H-1,2-benzothiazine-3-carboxamide 1,1-dioxide dissolved in 150 ml. of methylene chloride under a dry nitrogen atmosphere was treated with 2.63 g. (0.026 mole) of triethylamine (3.65 ml.). The resulting solution was then treated with a solution consisting of 4.2 g. (0.0131 mole) of 4-[N-methyl-N-($\beta$-phenylethyl)aminomethyl]benzoyl chloride hydrochloride (the product of Preparation U) dissolved in 50 ml. of methylene chloride, which was added in a portionwise manner. The resulting reaction solution was stirred at room temperature ($\sim 20°$ C.) for a period of 18 hours. The stirred reaction mixture was successively extracted two times with saturated aqueous sodium bicarbonate solution and one time with saturated aqueous sodium chloride, followed by drying of the organic layer over anhydrous sodium sulfate. After removal of the drying agent by filtration and the solvent by evaporation under reduced pressure, there was obtained a residual yellow foam. This residue was dissolved in 100 ml. of boiling isopropyl alcohol. The hot isopropyl alcohol solution was decanted away from a small amount of oil and then immersed in an ice-water bath, and the contents stirred vigorously to afford a solid precipitate. After a period of five minutes, the product was collected by filtration and then dried to ultimately afford 3.26 g. (43%) of pure 2-methyl-4-{4-[N-methyl-N-($\beta$-phenylethyl)aminomethyl]benzoyloxy}-N-(2-pyridinyl)-2H-1,2-benzothiazine-3-carboxamide 1,1-dioxide, m.p. 117°-120° C. The pure product was characterized by means of thin layer chromatography and infrared absorption spectra, in addition to elemental analysis.

Anal. Calcd. for $C_{32}H_{30}N_4O_5S$: C, 65.96; H, 5.19; N, 9.62. Found: C, 65.64; H, 5.23; N, 9.34.

EXAMPLE 12

A stirred solution consisting of 2.2 g. (0.0067 mole) of 4-hydroxy-2-methyl-N-(2-pyridinyl)-2H-1,2-benzothiazine-3-carboxamide 1,1-dioxide dissolved in 150 ml. of methylene chloride under a dry nitrogen atmosphere was treated with 1.59 g. (0.0157 mole) of triethylamine (2.2 ml.). The resulting solution was then treated with a solution consisting of 2.4 g. (0.008 mole) of 4-(N-methyl-N-cyclohexylaminomethyl)benzoyl chloride hydrochloride (the product of Preparation V) dissolved in 50 ml. of methylene chloride, which was added dropwise. The resulting reaction solution was stirred at room temperature ($\sim 20°$ C.) for 18 hours. The stirred reaction mixture was successively extracted two times with saturated aqueous sodium bicarbonate solution and one time with saturated aqueous sodium chloride, followed by drying of the organic layer over anhydrous magnesium sulfate. After removal of the drying agent by filtration and the solvent by evaporation under reduced pressure, there was obtained a white foam which was later recrystallized from ethyl acetate. The white crystalline material was filtered, washed with diethyl ether and dried to ultimately afford 2.10 g. (56%) of pure 4-[4-(N-methyl-N-cyclohexylaminomethyl)benzoyloxy]-N-(-2-pyridinyl)-2H-1,2-benzothiazine-3-carboxamide 1,1-dioxide, m.p. 164°-168° C. The pure product was characterized by means of thin layer chromatography and infrared absorption spectra, in addition to elemental analysis.

Anal. Calcd. for $C_{30}H_{32}N_4O_5S$: C, 64.26; H, 5.75; N, 10.00. Found: C, 63.89; H, 5.80; N, 9.81.

EXAMPLE 13

A stirred solution consisting of 790 mg. (0.0024 mole) of 4-hydroxy-2-methyl-N-(2-pyridinyl)-2H-1,2-benzothiazine-3-carboxamide 1,1-dioxide dissolved in 100 ml. of methylene chloride under a dry nitrogen atmosphere was treated with 575 mg. (0.0057 mole) of triethylamine (0.80 ml.). The resulting solution was then treated with 950 mg. (0.00287 mole) of 4-[N-methyl-N-(p-chlorophenyl)aminomethyl]benzoyl chloride hydrochloride (the product of Preparation W), which was added in a portionwise manner. The resulting reaction solution was stirred at room temperature ($\sim 20°$ C.) for 18 hours. The stirred reaction mixture was successively extracted two times with saturated aqueous sodium bicarbonate and one time with saturated aqueous sodium chloride, followed by drying of the organic layer over anhydrous sodium sulfate. After removal of the drying agent by filtration and the solvent by evaporation under reduced pressure, there was obtained a residual yellow foam. The residue was crystallized from ethyl acetate, filtered and washed with diethyl ether and then dried to ultimately give 850 mg. (50%) of pure 2-methyl-4-[4-(N- methyl-N-(p-chlorophenyl)aminomethylbenzoyloxy]-N-(2-pyridinyl)-2H-1,2-benzothiazine-3-carboxamide 1,1-dioxide as a quarter hydrate, m.p. 189°–191° C. The pure product was characterized by means of thin layer chromatography, gas chromatography and infrared absorption spectra, in addition to elemental analysis.

Anal. Calcd. for $C_{30}H_{25}ClN_4O_5S \cdot 0.25H_2O$: C, 60.70; H, 4.33; N, 9.44. Found: C, 60.48; H, 4.34; N, 9.48.

EXAMPLE 14

A stirred solution consisting of 1.49 g. (0.0045 mole) of 4-hydroxy-2-methyl-N-(2-pyridinyl)-2H-1,2-benzothiazine-3-carboxamide 1,1-dioxide dissolved in 30 ml. of methylene chloride under a dry nitrogen atmosphere was treated with 1.67 g. (0.0165 mole) of triethylamine (2.3 ml.). The resulting yellow solution was chilled in an ice-water bath, while a solution consisting of 1.53 g. (0.005 mole) of 4-[4-(N-methyl-N-(N',N'-dimethylcarbamylmethyl)aminomethyl]benzoyl chloride hydrochloride (the product of Preparation X) dissolved in 10 ml. of methylene chloride was added in a dropwise manner over a period of five minutes. The resulting reaction mixture was stirred at room temperature (~20° C.) for four hours. The stirred solution was successively extracted two times with 50 ml. of saturated aqueous sodium chloride. The organic layer was then dried over anhydrous sodium sulfate, filtered and the resulting filtrate concentrated in vacuo to give a residual tan foam. The residue was triturated with ca. 75 ml. of diethyl ether for a period of three hours and then filtered to give a beige solid (yield, 2.0 g.). The solid was dissolved in 75 ml. of ethyl acetate and filtered to remove a small amount of amorphous solid, followed by concentration of the filtrate to a volume of ca. 35 ml. After allowing the concentrated filtrate to cool in ice-water bath, there was obtained a beige solid which was collected by filtration and then dried to ultimately afford 900 mg. (35%) of pure 2-methyl-4-{4-[N-methyl-N-(N',N'-dimethylcarbamoylmethyl)aminomethyl]benzoyloxy}-N-(2-pyridinyl)-2H-1,2-benzothiazine-3-carboxamide 1,1-dioxide, m.p. 163° C. (decomp.). The pure product was characterized by means of mass spectroscopy, thin layer chromatography and infrared absorption spectra, in addition to elemental analysis.

Anal. Calcd. for $C_{28}H_{29}N_5O_6S$: C, 59.57, H, 5.19; N, 12.42. Found: C, 59.75; H, 5.34; N, 12.13.

EXAMPLE 15

A stirred solution consisting of 1.66 g. (0.005 mole) of 4-hydroxy-2-methyl-N-(2-pyridinyl)-2H-1,2-benzothiazine-3-carboxamide 1,1-dioxide dissolved in 45 ml. of methylene chloride under a dry nitrogen atmosphere was treated with 556 mg. (0.0055 mole) of triethylamine (0.77 ml.). The resulting yellow solution was cooled in an ice-water bath, while 1.47 g. (0.0055 mole) of 1-(4-chlorocarbonylbenzyl)pyridinium chloride (the product of Preparation Y) was added portionwise over a period of ten minutes. The resulting reaction mixture was stirred in the cold for a period of 30 minutes and then at room temperature (~20° C.) for 21.5 hours. The thick slurry which formed was filtered and washed with a small amount of methylene chloride to give 2.3 g. of a white solid material melting at 158°–178° C. (decomp.). The solid was recrystallized from 150 ml. of isopropanol and filtered to remove a small amount of white insolubles, followed by concentration of the resulting filtrate to a volume of ca. 125 ml. The resulting white crystalline material was then collected by filtration and dried to ultimately give 620 mg. (22%) of pure 2-methyl-4-[4-pyridiniummethyl)benzoyloxy]-N-(2-pyridinyl)-2H-1,2-benzothiazine-3-carboxamide 1,1-dioxide chloride, m.p. 190° C. (decomp.). The pure product was characterized by means of nuclear magnetic resonance data and infrared absorption spectra, in addition to elemental analysis.

Anal. Calcd. for $C_{28}H_{23}ClN_4O_5S$: C, 59.73; H, 4.12; N, 9.95. Found: C, 59.70; H, 4.22; N, 9.91.

I claim:

1. A compound of the formula:

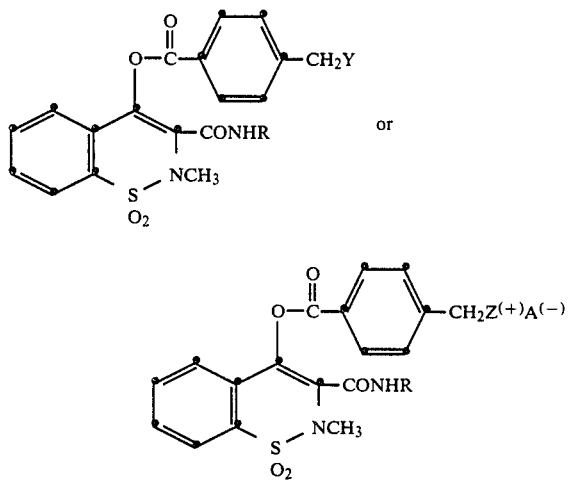

or a pharmaceutically acceptable acid addition salt thereof, wherein

R is 2-pyridyl, 6-methyl-2-pyridyl, 6-fluoro-2-pyridyl, 6-chloro-2-pyridyl, 5-methyl-3-isoxazolyl or 2-thiazolyl;

Y is N,N-dialkylamino having up to three carbon atoms in each alkyl moiety, N-methyl-N-benzylamino, N-ethyl-N-benzylamino, N-methyl-N-(β-phenylethyl)amino, N-ethyl-N-(β-phenylethyl)amino, N-methyl-N-cycloalkylamino and N-ethyl-N-cycloalkylamino each having up to six carbon atoms in the cycloalkyl moiety, N-methyl-N-phenylamino, N-ethyl-N-phenylamino, N-methyl-N-(p-chlorophenyl)amino, N-ethyl-N-(p-chlorophenyl)amino, N-methyl-N-(N',N'-dimethylcarbamylmethyl)amino, N-methyl-N-(N',N'-diethylcarbamylmethyl)amino, pyrrolidino, piperidino, 2-methylpiperidino, 2-ethylpiperidino, homopiperidino, 1-azacyclooctyl, N-methylpiperazino, morpholino or thiomorpholino;

Z is pyridinium, 2-methylpyridinium, 3-methylpyridinium, 4-methylpyridinium, 2,6-dimethylpyridinium, 2,4,6-trimethylpyridinium, 3-ethylpyridinium, 4-ethylpyridinium, 3-ethyl-4-methylpyridinium, 4-ethyl-2-methylpyridinium or 5-ethyl-2-methylpyridinium; and A is a pharmacologically acceptable anion.

2. A compound as claimed in claim 1 wherein R is 2-pyridyl.

3. A compound as claimed in claim 1 wherein R is 6-methyl-2-pyridyl.

4. A compound as claimed in claim 2 wherein Y is N,N-dialkylamino having up to three carbon atoms in each alkyl moiety.

5. A compound as claimed in claim 4 wherein Y is N,N-dimethylamino.

6. A compound as claimed in claim 4 wherein Y is N,N-diethylamino.

7. A compound as claimed in claim 2 wherein Y is N-methyl-N-(β-phenylethyl)amino.

8. A compound as claimed in claim 2 wherein Y is N-methyl-N-cycloalkylamino having up to six carbon atoms in the cycloalkyl moiety.

9. A compound as claimed in claim 8 wherein Y is N-methyl-N-cyclohexylamino.

10. A compound as claimed in claim 2 wherein Y is N-methyl-N-(p-chlorophenyl)amino.

11. A compound as claimed in claim 2 wherein Y is N-methyl-N-(N',N'-dimethylcarbamylmethyl)amino.

12. A compound as claimed in claim 2 wherein Y is piperidino.

13. A compound as claimed in claim 2 wherein Y is 2-ethylpiperidino.

14. A compound as claimed in claim 2 wherein Y is 1-azacyclooctyl.

15. A compound as claimed in claim 2 wherein Y is N-methylpiperazino.

16. A compound as claimed in claim 2 wherein Y is morpholino.

17. A compound as claimed in claim 2 wherein Z is pyridinium.

18. A compound as claimed in claim 3 wherein Y is piperidino.

19. A compound as claimed in claim 3 wherein Y is N-methylpiperazino.

20. A compound as claimed in claim 3 wherein Y is morpholino.

21. 2-Methyl-4-[4-(piperidinomethyl)benzoyloxy]-2H-1,2-benzothiazine-3-carboxamide 1,1-dioxide.

22. 2-Methyl-N-(6-methyl-2-pyridinyl)-4-[4-(piperidinomethyl)benzoyloxy]-2H-1,2-benzothiazine-3-carboxamide 1,1-dioxide.

23. An anti-arthritic composition comprising a pharmaceutically acceptable carrier and an effective anti-arthritic amount of a compound as claimed in claim 1.

24. A method for treating arthritic conditions in a warm-blooded animal, which comprises administering to said animal an effective anti-arthritic amount of a compound as claimed in claim 1.

* * * * *